US006099835A

United States Patent [19]
Kiczka

[11] Patent Number: 6,099,835
[45] Date of Patent: Aug. 8, 2000

[54] METHOD OF USING ANTIVIRAL COMPOSITION

[75] Inventor: Witold Kiczka, Princeton, N.J.

[73] Assignee: Nika Health Products Limited, Liechtenstein

[21] Appl. No.: 08/474,663

[22] Filed: Jun. 7, 1995

Related U.S. Application Data

[62] Division of application No. 07/865,002, Apr. 8, 1992, Pat. No. 5,466,449, which is a division of application No. 07/459,738, Jan. 26, 1990, Pat. No. 5,200,182.

[30] Foreign Application Priority Data

May 26, 1988 [WO] WIPO .................. PCT/US88/01785

[51] Int. Cl.$^7$ ................................................ A61K 38/47
[52] U.S. Cl. .................... 424/94.5; 424/94.6; 424/94.5
[58] Field of Search ............................... 424/94.61, 94.6, 424/94.5

[56] References Cited

U.S. PATENT DOCUMENTS

| | | | |
|---|---|---|---|
| 4,221,794 | 9/1980 | Simon et al. | 424/253 |
| 4,510,144 | 4/1985 | Hadden et al. | 514/257 |
| 4,739,046 | 4/1988 | DiLuzio | 536/117 |
| 4,744,984 | 5/1988 | Ragland | 424/92 |
| 5,200,182 | 4/1993 | Kiczka | 424/94.5 |
| 5,466,449 | 11/1995 | Kiczka | 424/94.61 |

FOREIGN PATENT DOCUMENTS

| | | |
|---|---|---|
| 0187705 | 7/1986 | European Pat. Off. . |
| 4020M | 4/1966 | France . |
| M6020 | 4/1966 | France . |
| 1092985 | 11/1967 | United Kingdom . |
| 1110504 | 4/1968 | United Kingdom . |
| 8911294 | 11/1989 | WIPO . |

OTHER PUBLICATIONS

Cavicchini, Minerva Med., vol. 75(9–10), pp. 457–462, 1984.
Zinsser Microbiology, 15Eder. Eds. Joklik et al., Appleton, 746–754, 1968.
Kooistra et al., Biochem. Biophy. Acta, vol. 631, pp. 439–450, 1980.
Bartholeyns et al., Euro. J. Cancer, vol. 15(4), pp. 85–91, 1979.
Bartholeyns et al., Archives Int'les de Physiologie et de Biochimie 87:155–222 (1979).
Massion, P.P. et al., Abstract from Am J Respir Cell Mol Biol 1993 Oct.;9(4):361–70.
Tashiro, M. et al., Abstract from J Virol 1985 Jan.;53(1):228–34.
Mochizuki, Y. et al., Abstract from J. Virol 1988 Aug.;62(8):3040–2.
Itoh, M. et al., Abstract from J Gen Virol 1987 Nov.;68(Pt 11):2939–44.
Ogura, H. et al., Abstract from J Gen Virol 1982 Aug.;61(Pt 2):207–15.
Hsu, M. et al., Abstract from Proc Natl Acad Sci USA 1984 Dec.;81(24):7732–6.
Tuffereau, C. et al., Abstract from Virology 1988 Feb.;162(2);417–26.
Lawton, P. et al., Abstract from Arch Virol 1986;89(1–4):225–33.
Lundh, B. et al., Abstract from Neuropathol Appl Neurobiol 1987 Mar.–Apr. 13(2):111–22.
Carthew, P. et al., Abstract from Br J Exp Pathol 1980 Apr.;61(2):172–5.
Kanda, T. et al., Abstract from Microbiol Immunol 1982;26(11):1045–55.
Benedetto, A. et al., Abstract from Virus Res 1986 Feb;4(2):117–32.
Tashiro, M. et al., Abstract from Arch Virol 1983;77(2–4):127–37.
Bartholeyns, Chem. Abs. 84:173704v, "Cytostatic properties . . . ", 1976.
Bartholeyns, Europ. J. Cancer vol. 15 pp. 85–91, 1979.
D'Alessio et al. Chem. Abs. 132193x, 1974 "Action of dimeric hybrids . . . ".
Tarnowski et al., Cancer Re. 36, Nov. 1976, pp. 4074–4078.
Cavicchini, S., "Use of high dose lysozyme . . . " Minerva Med., 75 (9–10), 1984, pp. 457–462.
Bartholeyns et al., "In vitro and In vivo Tumor Effect . . . ," Europ J. Cancer, vol. 15 (4), 1979 pp. 85–91.
Kooistra et al., "Effect of Size and Charge on Endocytosin . . . ", Biochimica et Brophysica Acta, 631 (1980), pp. 439–450.
Studebaker et al., JACS 93:18 Sep. 8, 1971, pp 4581–4585.
Bartholeyns et al., Chem. Abs. 197030w, 1989, "Effects of cross–linked . . . ".
Sorrentino et al., Europ. J. Biochem vol. 124 No. 1, 1982, pp. 183–189.
*The Biochemical Society*, "Effects of Cross–Linked Dimers of Ribonuclease A for of Lysozyme on the Processing of Endocytosed Peroxidase by Hepatoma Cells", J. Bartholeyns et al. vol. 202, 1982, 543–550.
Desoize, B. et al., "In vitro cytotoic activity . . . ", J. Pharm Pharmacol. vol. 38, (1986) pp. 8–13.
Ueda, Tadashi et al., An Intramolecular Cross–Linkage of Lysozyme . . . , Biochemistry, vol. 24 (1985) pp. 6316–6322.
Zinsser Microbiology, Ed. Joklik et al., Chapters 2 and 53, Publishers Appleton & Lange, 1992.

*Primary Examiner*—Chhaya D. Sayala
*Attorney, Agent, or Firm*—Ostrolenk, Faber, Gerb & Soffen, LLP

[57] ABSTRACT

A composition having antiviral and antibacterial effects is disclosed which comprises the dimeric forms of enzymes selected from lysozyme and ribonuclease and a pharmaceutically acceptable carrier. These dimeric forms are more effective in treating a variety of human and animal diseases because they are much less cytotoxic than the monomeric forms of the enzyme. A method for the use of these compositions is also disclosed which comprises applying an effective amount of the composition to the infected area.

9 Claims, No Drawings

METHOD OF USING ANTIVIRAL COMPOSITION

This is a division of application Ser. No. 07/865,002, filed Apr. 8, 1992 now U.S. Pat. No. 5,466,449, which is a division of application Ser. No. 07/459,738, filed Jan. 26, 1990, now U.S. Pat. No. 5,200,182.

FIELD OF THE INVENTION

The present invention relates to novel antiviral and antibacterial compositions comprising polymerized enzymes along with a pharmaceutically acceptable carrier, and a method for their use.

BACKGROUND OF THE INVENTION

The ever growing number of bacterial strains and viral diseases which are resistant to antibiotics have made it necessary to introduce new kinds of drugs in order to treat humans and animals. Among the many present treatments and medicines, it has been known to use enzymes in monomeric form in order to provide therapeutic effects in patients afflicted with various diseases. Enzymes are catalytically active proteins which perform almost all major life processes in organisms. Thus, many enzymes, either individually or in certain combinations, have been isolated for their physiocochemical, physiological, or biological effects.

Among the various enzymes or which certain therapeutic effects have been documented are lysozyme and ribonuclease. Lysozyme has been known since 1922, the year when it was discovered by Fleming. Only after 1950, however, were the enzymatic functions of lysozyme revealed. Since this time, the compound has been a subject of intense physiocochemical, physiologic and clinical research, but the extent of this compound's biological significance has still yet to be determined. Thus far, lysozyme has been observed to have various therapeutic properties, such as antiviral, antibacterial, anti-inflammatory and antihistaminic properties. The antibacterial effect appears to be based on the hydrolysis of the beta-1-4-glycoside bond between N-acetylomuraminic acid and N-acetyloglucosamine, both contained in the bacterial wall.

The presence of lysozyme in phagocytotic cells is also well documented. Research in this area has shown that the intracellular lysozyme contained in lysozymes is responsible for digesting the phagocytized bacteria. In humans, lysozyme has been observed to stimulate phagocytosis at a physiological concentration of 10–400 mg/ml.

Other properties of lysozyme have also been documented. For instance, it appears that lysozyme reduces body temperature during the infection process, where temperature is a response to endogenic pyrogens liberated by toxins. It also appears that lysozyme participates in immunological processes by stimulating the synthesis of gamma globulins, opsonins, and other antibodies. Still further, it has been suggested that lysozyme has a strong anti-inflammatory effect. Despite these known beneficial properties of lysozyme, despite numerous research projects and the production of pharmaceutical preparations based on lysozyme, the use of this enzyme for therapeutical purposes has been vastly limited.

Another group of enzymes which have been studied for their various biological effects are the ribonucleases. These are a group of enzymes commonly found in many animal and plant organisms as well as in bacterial cells. The study of their properties and research into methods of isolation was initiated in 1955 by Schmidt and McDonald. Among the findings based on this enzyme, it was found that in cancerous tissues the activity of ribonucleases was considerable reduced. For example, it was discovered that leukemogenic viruses drastically diminished the activity of acid ribonuclease in mice. Also, in mice with viral leukemia, a considerable decrease in acid ribonuclease activity was found in mitochondria and microsome fractions obtained from the spleen tissue of those animals.

The studies cited above suggest that the decrease in activity of ribonuclease is somehow closely connected with the infections caused by the virus. It has thus been suggested that the ribonuclease enzymes may possess some antiviral activity. Again, however, at present, there have been no known reports on the preparation of compounds employing this enzyme as an antiviral agent.

One of the main reasons why such potentially beneficial enzymes have not as yet been widely used for their therapeutic effects is the observed cytotoxic effect of the monomeric forms of these and other enzymes. In tests with cultured fibroblasts, there has been an observed cytotoxic effect from both the lysozyme and ribonuclease monomers at even very small quantities. Clearly, the potential beneficial effects from these and other enzymes could be achieved if an effective way of controlling these cytotoxic effects could be developed. What is desired, therefore, is to develop compositions based on lysozyme, ribonuclease, or other similar enzymes, which can effectively be used to treat viral or bacterial disease or other harmful conditions without the cytotoxic effects normally observed when the enzymes are used in the monomeric form.

SUMMARY OF THE INVENTION

In accordance with the present invention, it has been discovered that an antiviral or antibacterial composition having as its active ingredient lysozyme or ribonuclease, yet which does not exhibit cytotoxic effects can be prepared by using the dimeric forms of these enzymes. By preparing compositions using as the active ingredient a lysozyme or ribonuclease dimer and a pharmaceutically acceptable carrier, a number of infectious diseases can be successfully treated without appreciable cytotoxic effects.

DETAILED DESCRIPTION OF THE PREFERRED EMBODIMENTS

The antiviral and antibacterial compositions of the present invention can be prepared by first obtaining lysozyme and ribonuclease in their monomeric form. The lysozyme monomers (Catalog No. 28260) and ribonuclease monomers (Catalog No. 34388) used in the preparation of compounds prepared in accordance with the present invention, were obtained from Serva Feine Biochemica, Gmbh und Cooperation, D69-000, Heidelberg. These enzyme monomers can be polymerized into dimers by any conventional method currently used in the art. However, particularly preferred, is the enzyme polymerization carried out and disclosed in Carlsson et al, *Biochemistry Journal*, 173: 723–737 (1978). Other methods, such as that described in Sorrentino et al., *Eur. J. Biochem.* 124: 183–9 (1982), can also be utilized. It has also been observed that a particularly useful ribonuclease dimer which can be employed in the compositions of the present invention is a dimer prepared from pancreatic ribonuclease A, isolated from animal pancreatic tissues.

It has been observed that compositions containing as the active ingredient a lysozyme or ribonuclease dimer and a pharmaceutically acceptable carrier are effective in treating a variety of bacterial and viral diseases without undesirable cytotoxic effects. These potentially harmful effects of the enzymes were tested in comparative studies using both the monomeric and dimeric forms of lysozyme and ribonuclease. In these studies, various concentrations of monomers and dimers of lysozyme and ribonuclease were administered to cultures of green monkey kidney (GMK) fibroblasts. It was observed that the lysozyme monomer proved to be cytotoxic to fibroblasts after 24 hours at concentrations of 0.1 mg/ml and 1.0 mg/ml. After three days of incubation, a cytotoxic effect on fibroblasts was observed even at a concentration of 0.01 mg/ml, which affected 50% of the incubated cells. After five days, 75% of the cultivated cells were affected by the cytotoxic activity of the lysozyme monomer at concentrations of 1.0 and 0.1 mg/ml. Comparatively, the lysozyme dimer showed no cytotoxic effect in any concentration used in these tests, not even after a seven day period. These studies showed that the dimeric form of lysozyme was approximately 100 times less toxic to GMK fibroblasts than the monomeric form.

The study with regard to ribonuclease showed a similar lack of cytotoxic effect for the dimeric form. In the study, ribonuclease proved to be cytotoxic to GMK fibroblasts in a five day culture for concentrations as low as 0.0001 mg/ml. After seven days of culture, cytotoxic effects of the ribonuclease monomers at concentrations of 0.01 mg/ml and above eliminated 100% of the cultivated cells. As a contrast, the ribonuclease dimer showed no cytotoxic effects whatsoever on the GMK fibroblasts at all concentration levels, not even after a seven-day incubation. The dimeric form of ribonuclease therefore, was observed to be approximately 1,000–10,000 times less toxic to the fibroblasts than the monomeric form. These tests clearly showed that the cytotoxic effects which normally accompany use of the monomeric forms of enzymes such as lysozyme and ribonuclease could be virtually eliminated if those enzymes were utilized in their dimeric forms.

Further research has shown that despite the lack of appreciable cytotoxic effects, lysozyme and ribonuclease in their dimeric form can be extremely effective in treating viral and bacterial infections. In tests involving fertilized hen eggs and a Sendai virus strain, lysozyme dimer was intraamniotically injected into eggs at various concentrations. Into each egg was also injected two units of the Sendai virus. After incubation, the amniotic and allantoic fluids were collected from infected and control eggs and compared. These tests indicated that the lysozyme dimer was able to inhibit the replication of the Sendai virus cultivated in ten day old fertilized hen eggs, even at a concentration as low as 0.01 mg/ml. Similar tests using lysozyme and ribonuclease dimers have shown a bacteriostatic effect of these dimeric enzymes on strains of Streptococcus bacteria.

Compositions prepared from lysozyme or ribonuclease dimers in accordance with the present invention, therefore, can be used to treat a variety of viral and bacterial infections. The compositions can be prepared in a variety of forms, and administration of these enzyme-carrier compositions can be carried out internally or externally for a particular human or animal patient depending on the disease that needs to be treated. For internal diseases, such as ear infection, mastitis, stomach or vaginal tract infections, the dimeric compositions of the invention can be suitably prepared and administered orally, intravenously, parenterally, via a suppository, or any other method which will enable the dimeric solution to reach the infected area. For external conditions, such as viral or bacterial skin disease, infected wounds, or herpes or other sexual diseases with external effects, the compositions of the invention can be administered topically to the patient in any of a variety of suitable forms.

The particular nature of the diseases or infection treated, therefore, will determine the proper form for the composition of the present invention. For external treatments, the composition can be administered in such various forms as ointments, lotions, solutions, oils, etc. Where an internal application is necessary, a number of suitable forms such as drops, tablets, solutions, capsules, dentrifices, etc. can be employed. The particular form of the composition as applied to the patient will also thus determine the nature of the pharmaceutically acceptable carrier used in the dimeric enzyme composition. Among the many suitable carriers which can be used are hydrophilic bases, physiologically acceptable salt solutions, water, ointments, powders, etc.

Enzymatic treatment of viral or bacterial infections without cytotoxic effects is thus provided in the present invention by administering to a human or animal patient an effective amount of the dimeric compositions discussed above. By effective amount is meant that amount which is necessary to produce antiviral or antibacterial effects. The amount needed to effect treatment will vary in each case depending on the nature of the disease treated and the form of the dimeric composition provided. In general, the composition of the present invention is administered at a dosage level of from 0.1 to 5.0 mg/kg of body weight, with a range of 1.0 to 2.0 mg/kg/body weight particularly preferred. In the case of topical treatment, ointments prepared using 4–20 mg of the dimer in approximately 200 ml of a solution of water, paraffin and propylene glycol has been effective if applied 4–5 times per day. Dosages in these ranges should be sufficient to treat a number of viral or bacterial diseases without the harmful cytotoxic effects that would accompany treatments with enzyme monomers.

The following examples are presented as illustrative only of the present invention and are not intended to limit its scope in any way:

EXAMPLE 1

Comparative research was carried out concerning the cytotoxic effect of monomers and dimers of lysozyme and pancreatic ribonuclease A on a culture of green monkey kidney (GMK) fibroblasts. These tests were carried out by applying monomers and dimers to the fibroblast culture at concentrations of 0.0001 to 1.0 mg/ml. The cultures were then incubated for seven days, after which the cultures were examined for cytotoxicity. The results of these tests are presented in Tables 1 and 2.

As can be observed from Table 1, the lysozyme monomer proved to be cytotoxic to fibroblasts after 24 hours at concentrations of 0.1 mg/ml and 1.0 mg/ml. After three days of incubation, the monomer showed cytotoxic effects on fibroblasts even at a concentration of 0.01 mg/ml, affecting 50% of the incubated cells. After five days, 75% of the cultivated cells were affected by the cytotoxic activity of the lysozyme monomer at concentrations of 1.0 mg/ml and 0.1 mg/ml.

In contrast, the dimeric form of lysozyme showed no cytotoxic effect in any concentration used in the test even after completion of the seven day incubation. The studies thus showed that the lysozyme dimer proved to be about 100 times less toxic to GMK fibroblasts than the lysozyme monomer.

As can be observed in Table 2, the monomer of pancreatic ribonuclease A proved to be cytotoxic to GMK fibroblasts in the five day culture even at concentrations as low as 0.0001 mg/ml. After seven days of culturing, the cytotoxic effect of pancreatic ribonuclease A at concentrations of 0.01 mg/ml and above was of sufficient strength to eliminate 100% of the cultivated cells.

As was similar to the case with the lysozyme dimer, the dimeric form of pancreatic ribonuclease A showed no cytotoxic effect on GMK fibroblasts at any concentration used in the test for the duration of the seven day period. The results thus indicated that the dimer of pancreatic ribonuclease A was about 1,000 to 10,000 times less toxic to GMK fibroblasts than the pancreatic ribonuclease A monomer.

TABLE 1

Tests for cytotoxicity of MONOMER of lysozyme and DIMER of lysozyme

| Type of Preparation | Conc. mg/ml | After 24 hr | After 3 days | After 5 days | After 7 days |
|---|---|---|---|---|---|
| Control | | | 0 | 0 | 0 |
| Lysozyme MONOMER | 1.0 | 2 | 2 | 3 | 3 |
| | 0.1 | 1 | 2 | 3 | 3 |
| | 0.01 | 0 | 2 | 2 | 2 |
| | 0.001 | 0 | 0 | 0 | 0 |
| | 0.0001 | 0 | 0 | 0 | 0 |
| Lysozyme DIMER | 1.0 | 0 | 0 | 0 | 0 |
| | 0.1 | 0 | 0 | 0 | 0 |
| | 0.01 | 0 | 0 | 0 | 0 |
| | 0.001 | 0 | 0 | 0 | 0 |
| | 0.0001 | 0 | 0 | 0 | 0 |

The tests were performed 3x on a culture of GMK/green monkey kidney/fibroblasts.
0 - cytotoxicity = 0%
1 - cytotoxicity = 25%
2 - cytotoxicity = 50%
3 - cytotoxicity = 75%
4 - cytotoxicity = 100%

TABLE 2

Tests for cytotoxicity of pancreatic ribonuclease A MONOMER and pancreatic ribonuclease A DIMER

| Type of Preparation | Conc. mg/ml | After 24 hr | After 3 days | After 5 days | After 7 days |
|---|---|---|---|---|---|
| Control | | | 0 | 0 | 0 |
| Pancreatic ribonuclease A MONOMER | 1.0 | 1 | 2 | 4 | 4 |
| | 0.1 | 0 | 1 | 3 | 4 |
| | 0.01 | 0 | 0 | 3 | 4 |
| | 0.001 | 0 | 0 | 2 | 3 |
| | 0.0001 | 0 | 1 | 1 | 2 |
| Pancreatic ribonuclease A DIMER | 1.0 | 0 | 0 | 0 | 0 |
| | 0.1 | 0 | 0 | 0 | 0 |
| | 0.01 | 0 | 0 | 0 | 0 |
| | 0.001 | 0 | 0 | 0 | 0 |

The test was performed 3x on a culture of GMK/green monkey kidney/fibroblasts.
0 - cytotoxicity = 0%
1 - cytotoxicity = 25%
2 - cytotoxicity = 50%
3 - cytotoxicity = 75%
4 - cytotoxicity = 100%

EXAMPLE 2

The dimer of lysozyme was studied with regard to its antiviral effects. In the experiments, lysozyme dimer was injected into ten day-old fertilized hen eggs in concentrations of 10.0 mg/ml, 1.0 mg/ml, 0.1 mg/ml, 0.01 mg/ml and 0.001 mg/ml. A Sendai virus strain (hemagglutinational titre=1:128 HA) was added to each concentration of the dimer in an amount of two hemagglutinational units. After administration of the lysozyme dimer and the virus, the eggs were incubated for 72 hours at 37° C. After the incubation period, the amniotic and allantoic liquids were collected from the infected eggs and subject to a hemagglutination test by means of micromethods with the use of a Takatsy set and hen blood corpuscles. The experiments were then repeated. The results obtained in these experimental trials are presented in Table 3. As can be observed from Table 3, the lysozyme dimer inhibited the replication of Sendai virus cultivated in ten day-old fertilized hen eggs, even at concentrations as low as 0.01 mg/ml.

TABLE 3

The effect of lysozyme DIMER on Sendai virus strain.

TABLE 3

The effect of lysozyme DIMER on Sendai virus strain.

| Concentration of lysozyme DIMER in mg/ml | Hemagglutination inhibition/ hemagglutination test on hen red blood cells according to Takatsy method | |
|---|---|---|
| | September 1987 | November 1987 |
| 10.0 | +++ | not investigated |
| 1.0 | +++ | +++ |
| 0.1 | +++ | +++ |
| 0.01 | +++ | +++ |
| 0.001 | ++ | no inhibition |

+++ - full inhibition, 1:256
++ - limited inhibition, 1:32

1. Tests were performed on Sendai virus strain. The viral hemagglutination titre was 1:128 HA.
2. 10 day-old, fertilized hen eggs served as an experimental model.
3. An identical quantity of Sendai virus—2 hemagglutinational units—was added to each concentration of lysozyme DIMER. At the same time a control test for lysozyme DIMER was initiated in order to find out if it has hemagglutinational properties—the result was negative. Consecutive concentrations of lysozyme DIMER plus 22 HA units of the virus were then used to infect intraamniotically 4 hen eggs. The eggs were incubated for 72 hours at 37° C.
4. After the incubation period, the amniotic and allantoic fluids were collected from the infected eggs. A hemagglutinational test was performed (hemagglutinational micromethod) with the use of Takatsy test set and hen red blood cells.

EXAMPLE 3

The effects of the dimeric forms of lysozyme and pancreatic ribonuclease A on bacteria were tested on several pathogenic strains collected from cows with mastitis. The effect of different concentrations of lysozyme dimer on three strains (Streptococcus agalactiae, S. dysgalactiae and S. liberis) are presented in Table 4. These test results showed that all three of the Streptococcus strains proved to be sensitive to the activity of the lysozyme dimer. This was most evident in the case of S. liberis which was affected by the activity of the dimer at a concentration as low as 1.25 mg/ml. Bacteriostatic effects on the other strains of Streptococcus were observed at concentrations starting at about 10 mg/ml.

In Table 5, the effects of pancreatic ribonuclease A dimer and lysozyme dimers on pathogenic bacteria strains cultivated from human patients is presented. As can be observed from the table, pancreatic ribonuclease A dimer was most effective on bacterial strains of *Pseudomonas aeruginosa, Escherichia coli* and *Proteus vulgarus*, particularly at a concentration ranging of from about 5 to 10 mg/ml. Bacterial strains of Staphylococcus and Streptococcus were found to be sensitive to the lysozyme dimer, also at concentrations of about 5 to 10 mg/ml. Sensitivity tests were performed in accordance with generally accepted international principles recommended by the WHO.

EXAMPLE 4

The effect of the lysozyme dimer and the pancreatic ribonuclease A dimer on the proliferation of K-562 Erythroleukemic cell lines was determined by

TABLE 4

MIC—Minimal Inhibitory Concentration of lysozyme DIMER IN mg/ml—Bacterial strains were cultivated on samples collected from cows with mastitis

TABLE 4

MIC - Minimal Inhibitory Concentration of lysozyme DIMER IN mg/ml - Bacterial strains were cultivated on samples collected from cows with mastitis

| Bacterial Strains | Lysozyme DIMER in mg/ml | | | | |
|---|---|---|---|---|---|
| | 1.25 | 2.5 | 5.0 | 10.0 | 20.0 |
| *Streptococcus agalactiae* | + | + | + | − | − |
| *Streptococcus dysgalactiae* | + | + | + | − | − |
| *Streptococcus liberis* | − | − | − | − | − |

− = no proliferation of bacteria
+ = proliferation of bacteria

−=no proliferation of bacteria
+=proliferation of bacteria

Sensitivity tests were performed in accordance with generally accepted international principles recommended by the WHO.

TABLE 5

MIC—Minimal Inhibitory Concentration of pancreatic ribonuclease A DIMER in mg/ml Bacterial strains were cultivated on samples collected from patients.

TABLE 5

MIC - Minimal Inhibitory Concentration of pancreatic ribonuclease A DIMER in mg/ml Bacterial strains were cultivated on samples collected from patients.

| Bacterial strains | Pancreatic ribonuclease A DIMER in mg/ml | | | | Lysozyme DIMER in mg/ml | | | |
|---|---|---|---|---|---|---|---|---|
| | 2.5 | 5.0 | 10.1 | 20.0 | 2.5 | 5.0 | 10.0 | 20.0 |
| *Pseudomonas aeruginosa* | + | − | − | − | + | + | + | + |
| *Escherichia coli* | + | + | − | − | + | + | + | + |
| *Proteus vulgaris* | + | + | − | − | + | + | + | + |
| Staph.aureus/Standard strain 209/ | + | + | + | + | + | − | − | − |
| Staph.aureus/pathogenic strain from patients | + | + | + | + | + | − | − | − |

TABLE 5-continued

MIC - Minimal Inhibitory Concentration of pancreatic ribonuclease A DIMER in mg/ml Bacterial strains were cultivated on samples collected from patients.

| Bacterial strains | Pancreatic ribonuclease A DIMER in mg/ml | | | | Lysozyme DIMER in mg/ml | | | |
|---|---|---|---|---|---|---|---|---|
| | 2.5 | 5.0 | 10.1 | 20.0 | 2.5 | 5.0 | 10.0 | 20.0 |
| Staph.aureus MRSA strain nr 11704 | + | + | + | + | + | + | − | − |
| Staph.aureus MRSA strain nr 11708 | + | + | + | + | + | + | − | − |
| Strept.pyogenes pathogenic strain from patient | + | + | + | + | + | − | − | − |

− = no proliferation of bacteria
+ = proliferation of bacteria
MSRA - Methicilin Resistent Staphylococcus aureus. Strains collected from patients. Sensitivity tests were performed in accordance with generally accepted international principles recommended by the WHO.

−=no proliferation of bacteria
+=proliferation of bacteria
MSRA—Methicilin Resistent *Staphylococcus aureus*. Strains collected from patients. Sensitivity tests were performed in accordance with generally accepted international principles recommended by the WHO.

TABLE 6

The effect of lysozyme DIMER on the proliferation of K-562 erythroleukemic cell lines. Cells of K-562 line were used at a concentration of $10^5$ ml. The effect was estimated after 24 hours of culture at 37° C. and with a 5% $CO_2$ flow.

TABLE 6

The effect of lysozyme DIMER on the proliferation of K-562 erythroleukemic cell lines. Cells of K-562 line were used at a concentration of $10^5$ ml. The effect was estimated after 24 hours of culture at 37° C. and with a 5% $CO_2$ flow.

| Concentration lysozyme DIMER in mg/ml | Proliferation of K-562 cells in 24 hours in vitro culture | |
|---|---|---|
| | Number of Cells | Percentage of Dead Cells |
| Control | 190,000 | 2–3% |
| 1.0 | lysis of cells | 100% |
| 0.1 | 107,000 | 95% |
| 0.05 | 98,000 | 99% |

TABLE 7

The effect of pancreatic ribonuclease A DIMER on the proliferation of K-562 erythroleucemic cell lines. Cells of K-562 line were used at a concentration of $10^5$ ml. The effect was estimated after 24 hours of culture at 37° C. and with a 5% $CO_2$ flow.

TABLE 7

The effect of pancreatic ribonuclease A DIMER on
the proliferation of K-562 erythroleucemic cell
lines. Cells of K-562 line were used at a
concentration of $10^5$ ml. The effect was
estimated after 24 hours of culture at
37° C. and with a 5% $CO_2$ flow.

| Concentration of pancreatic ribonuclease A DIMER | Proliferation of K-562 cells in 24 hours in vitro culture | |
|---|---|---|
| | Number of Cells | Percentage of Dead Cells |
| Control | 207,000 | 2–5 |
| 1.0 | 68,000 | 74 |
| 0.1 | 140,000 | 14 |
| 0.05 | 150,000 | 7 | applying various concentrations of the dimers to cells from these lines. The results of these tests are presented in Tables 6 and 7. In short, all concentrations of the lysozyme dimer used in the experiment showed strong cytopathogenic effects on the K-562 cells. Additionally, as can be observed in Table 7, the pancreatic ribonuclease A dimer also had a similar effect on the Erythroleukemic cell line, but only at concentrations of 1.0 mg/ml.

EXAMPLE 5

The effect of lysozyme dimer on purulent otitis media in dogs was examined. The study was undertaken using 19 dogs of different races with various forms of the disease. The disease was characterized by an inflammatory process which on average lasted for about 7–14 days, but in one case lasted for nine months. In seven of the dogs, the purulent discharge from the inflamed ear was examined for an identification of bacterial strains therein before treatment was undertaken. These culturing tests showed the presence of Staphlococcus germs, blue pusbacillis, *Pseudomonas aeruginosa*, Coccidia species, and various bacilli species.

The afflicted dogs manifested various signs that they were in pain, such as shaking their heads and trying to reach the infected ear with their paws. The dogs generally had impaired appetites and heightened temperatures (39.2–41.2° C.). Eighteen of the dogs in the study had not been given any previous treatment with any pharmacological means. One dog, in which the infection had persisted for nine months, had been given several antibiotics, but these had not been effective in treating the condition.

The dogs were treated with a composition of the present invention which consisted of a solution of 20 mg of lysozyme dimer and 25 ml of physiological salt. The composition was applied in the form of drops, and ten drops were placed into the inflamed ear four–five times a day. After the first day of treatment, a marked improvement was already observed: temperatures dropped, the dogs apparently felt more comfortable, and had better appetites. The symptoms of purulent inflammation receded fully between the third and sixth day of the treatment. In the dog which had been previously treated with antibiotics unsuccessfully for nine months, successful recession of the disease was achieved after ten days. Lysozyme dimer was thus shown to be effective in treating purulent otitis media in dogs.

EXAMPLE 6

The effects of lysozyme dimer on cows with mastitis was examined. Six cows with mastitis were used in the study. These cows showed signs of the disease such as temperatures above 40.5° C. and an impaired appetite. In all six cases, the treatment began on the second day of the disease. Before the compositions were administered, samples of milk were collected for bacterial examination. The cultures were observed to contain microbes such as Staphlococcus and *Streptococcus agalactiae.*

Lysozyme dimer was given to each cow through syringe injection in the infected teats at a dosage of 40 mg in a solution of 50 ml of physiological salt twice a day. It was found that after only 24 hours, the body temperature was normal again, and the appetite returned. After three days, all cows under treatment showed no symptoms of the disease. The treatment was thus only continued up to four days, after which examination of the milk showed that the pathogenic microbes found before treatment had disappeared. Further, no changes were found in the milk that would indicate a subclinical mastitis. In none of the treated cows was there found a decrease in milk yield, nor was the patency of teats impaired. After 24 hours of the lysozyme dimer treatment, no blocking substances were found in the milk of the treated cows. The quick disappearance of disease symptoms, as well as full retention of milking capacity thus indicates that the lysozyme dimer compositions of the present invention may be used successfully in the treatment of bovine mastitis. This treatment will be of particular economic importance for preventing mastitic infections caused by Staphlococcus and Streptococcus bacterial strains, which currently cost the dairy industry approximately $5.4 billion a year.

EXAMPLE 7

Canine parvovirus (CPV) infection was treated by oral administration of lysozyme dimer. In twenty-seven dogs of different races and weight, aged from three months to six years, veterinary surgeons found a symptom complex typical for parvovirus infection. All animals in the tests had high temperatures (40–41.6° C.), frequent paroxysms of profuse vomiting, numerous and characteristically fetid diarrhea stools, as well as symptoms of dehydration and apathy. The animals also gave impressions of intense suffering. Treatment began on the average between the third and fifth day of infection, depending on how soon an animal's owner brought the pet to the veterinary station. The infected dogs were give lysozyme dimer at a dose of 1–2 mg per kg of body weight two times a day. To animals which were still able to drink, the lysozyme dimer was administered in drinking water. Animals unable to drink were given the preparation through a probe in a solution of physiological salt.

Of the twenty-seven dogs under treatment, twenty-five dogs regained full physical fitness after 3–5 days of treatment. Typically, even during the first day, there was observed a marked decrease in the number of stools and attacks of vomiting, and in the majority of the dogs these symptoms receded totally after two days of treatment. In a few dogs, these symptoms disappeared even after the first dose of the preparation. No side effects connected with the administration of the lysozyme dimer composition were observed in any animal. These clinical tests show that the lysozyme dimer composition of the invention may be successfully used on dogs with parvovirus infection.

EXAMPLE 8

The effects of the lysozyme dimer composition of the present invention on certain dermatological diseases in humans were examined. Tests were carried out with several dozen human patients aged from 15 to 35 and suffering from various skin diseases which had been previously but unsuccessfully treated with conventional methods. The following diseases were identified in this group:
1 Forunculosis chronica—2 cases
2 Sycosis barbae—1 case
3 Impetigo contagiosa—11 cases
4 Acne vulgaris—22 cases
5 Resacea—6 cases
6 Varicose ulcer—12 cases In some of the patients from this group, the treatment was preceded by bacteriological culture tests. In most cases, *Staphlococcus aureus* was cultivated from the collected material. The treatment consisted in administering four times a day an ointment containing 20 mg of lysozyme dimer. A particularly preferred formula for the ointment is as follows:

| Lysozyme dimer | 20.0 mg |
| Acetylstearoyloxy alcohol | 25.0 mg |
| Paraffin liquidum | 10.0 mg |
| Span 60 | 5.0 mg |
| Tween 60 | 8.0 mg |
| Propylene glycol | 10.0 mg |
| Aseptina M | 0.3 mg |
| Aseptina P | 0.16 mg |
| Distilled water | 200.0 ml |

In all patients, the various skin conditions disappeared within 10–12 days, and in some cases clearing was observed after 3 days. In patients with chronic Forunculosis, the treatments lasted up to 4–5 weeks, and those with varicose ulcer generally took from 2–12 weeks to recover depending on how severe the skin condition was, and how long the disease had developed before the treatment. The results obtained in this study suggests that lysozyme dimer may be used successfully for a variety of skin diseases.

EXAMPLE 9

Various infectious diseases of the genital region were treated using a lysozyme dimer composition of the present invention. Nine women, aged from 25–49 were treated in these tests, seven patients having Colpitis chronica, one patient having Douglas' abscess, and one with Bartholinitis. The patients with Colpitis chrorica were given intra-vaginal suppositories containing 10 mg of lysozyme dimer in 2 ccm of hydrophilic base. The suppositories were administered two times a day, for a period of 7 days. In all patients, there was observed a total recession of the inflammation of the genital area. In addition, leucorrhea and other symptoms disappeared as well. The patient with Douglas' abscess was given 20 mg of lysozyme dimer in 5 ml of 0.9% NaCl solution two times a day over a span of 4 days. The solution was applied directly into the Douglas' cavity. Before each administration of lysozyme dimer, purulent content was aspired from the Douglas' cavity. These cultures indicated the presence of *Streptococcus haemolyticus* and *bacterium coli*. The patient's abnormally high body temperature was reduced to normal values within 24 hours after the first administration of lysozyme dimer. Pain symptoms as well receded during this time. On the fourth day after the second administration of the lysozyme dimer composition, no pus was found in Douglas' cavity. In this case, there was a reoccurrence of the disease after three weeks, but another two doses of lysozyme dimer administered into the Douglas' cavity was able to bring the disease process under control.

The patient with Bartholinitis was treated with one dose of 20 mg of lysozyme dimer in 1 ccm of 0.9% NaCl, which was administered immediately into the suppurated gland, after the aspiration of purulent content from it. After 4 days, this patient was found to be completely cured. During 4 months of subsequent observations, there were no reoccurrences of this disease. These clinical tests indicate that lysozyme dimer has an extremely beneficial therapeutic effect in cases of certain infectious diseases of the genital region in women. Additionally, it appears that it will be possible to treat local abscess by administering lysozyme dimer immediately into the cavities with purulent content.

EXAMPLE 10

Effect of a lysozyme dimer solution on infected wounds was studied. In this group, there were 4 patients with infected post-operative wounds; 2 women after laparotomy, one woman after toe amputation due to nucrosis in the course of diabetic angiopathy, and one man after amputation of lower extremity due to Burger's disease. In all cases, moist applications and lavations with a solution of lysozyme dimer in 5 ml of 0.9% NaCl were given four times a day. In the patients with suppurating wounds after laparotomy, complete cure was effected after 4 and 6 day periods. In the other patients, cure was effected after 21 days and 5 months, respectfully. These tests indicate that lysozyme dimer may be used as a therapeutic means without side effects in the treatment of infected post-operative wounds.

EXAMPLE 11

Clinical observations were made on patients with Herpes genitalis treated with a ribonuclease A dimer composition. The study group included five patients who were women aged from 23–36 years old. Four of them had developed the disease for the first time, while one of the women had the disease for the third time. All patients were in the period of blistering, which is normally between the third and fifth day of the disease, and complained of very strong pain in the perineal region, particularly during urination. In all patients, we found swelling and infection of labia as well as numerous blisters filled with turbid fluid on mucous labial membranes and on the external skin of the thigh and anal regions. In all patients the inguinal lymphatic nodules were enlarged and painful.

The treatment involved application of an ointment containing the dimer of ribonuclease A four to five times daily on blisters and infected areas of mucous membrane. The ointment applied had the following formula:

| Ribonuclease dimer | 20.0 mg |
| Acetystearoyloxy alcohol | 25.0 mg |
| Paraffin liquidum | 10.0 mg |
| Span 60 | 5.0 mg |
| Tween 60 | 8.0 mg |
| Propylene glycol | 10.0 mg |
| Aseptina M | 0.3 mg |
| Aseptina P | 0.16 mg |
| Distilled water | 200.0 ml |

The patients receiving the dimer treatment reported that after several minutes and at least within one hour since the first application of the ointment, pain diminished substantially, and disappeared totally over the next 10–20 hours. Physical examination showed that in four patients, pathological changes receded totally after three days of treatment. In the other patient, pathological conditions were totally eliminated after five days. In none of these patients did new blisters emerge after the application of the ointment containing pancreatic ribonuclease A dimer. The above study shows that ointments containing dimers of the present invention can be used as a successful treatment for Herpes genitalis.

EXAMPLE 12

More than 100 patients of various ages were treated for labial herpes using compositions of the present invention. In all of these patients, symptoms included swelling of the upper lip region, reddening and numerous blisters filled with turbid fluid. All patients complained of pain in the skin in areas affected by the disease, and in addition there was a sensation of tension in the tissues. Treatment involved application locally, for four to five times daily, of an ointment containing pancreatic ribonuclease A dimer.

All of the patients treated without exception stated that pain and tension of tissues quickly receded. A total recession of pain followed within the next several hours, as was observed in the cases involving genital herpes. Physical examinations showed that the swelling and blisters disappeared within 2–3 days. In individual cases, it took up to five days for the conditions to completely clear and for the entire healing process to be accomplished. It was further observed that in patients whose treatment started on the first day of the disease, skin conditions such as swelling, irritations, and papules disappeared totally after 24 hours. Another observation was that persons suffering frequent reoccurrences of this disease had prolonged periods between reoccurrences and that the reoccurring symptoms were milder each time. In no cases were any side effects observed.

EXAMPLE 13

Clinical research was done on six patients with herpes zoster who were treated with a dimer composition of the present invention. In five cases, the disease developed in a typical manner, and the sixth case had particular complications which will be discussed below. These patients were treated with an ointment containing pancreatic ribonuclease A dimer, and the treatment was begun on the third or fourth day of the disease. Applications of the ointment were made 4–5 times daily.

In all cases, pain receded totally within the first 24–48 hours. Blisters were observed to dry up after 3–4 days, and thus after this period it was decided to terminate the treatments. Within the next few days, the skin conditions healed completely. In none of the patients did the pain persist after around the first 24–48 hours, and conditions did not reappear in three patients remaining under observation for more than one year. In one patient, as indicated above, there was an unusual clinical development of the disease. A woman aged 42 had been treated for lung cancer using cobalt therapy which had seriously impaired her immunity system. Apart from the usual symptoms of herpes zoster, there was found a generalized dissemination of blisters all over her body. The treatment using the ribonuclease dimer composition of the present invention was totally successful in this immunity-impaired patient, and the woman showed complete recession of the blister condition after a few days. The successful results in this patient and in the other members of the group shows the particular effectiveness of pancreatic ribonuclease A dimer against herpes zoster caused by Varicella viruses.

What is claimed is:

1. A method of treating viral infections comprising administering to a human or animal subject in need of such treatment an effective antiviral amount of a dimer of lysozyme and a pharmaceutically acceptable carrier.

2. A method according to claim 1 wherein the composition is administered orally, intravenously or topically.

3. A method according to claim 1 wherein the carrier is a physiologically acceptable salt solution.

4. A method according to claim 3 wherein said salt solution of a 0.5–1.5% salt solution in water.

5. A method according to claim 1 wherein the effective amount of lysozyme dimer is from 0.1 to 5 mg/kg of body weight.

6. A method according to claim 5 wherein the effective amount is 1 to 2 mg/kg of body weight.

7. A method according to claim 1 for treating infection caused by parvovirus.

8. A method according to claim 1 wherein lysozyme dimer is administered in a concentration of 0.001 to 10 mg/ml.

9. A method according to claim 1, for inhibiting the replication of Sendai virus.

* * * * *